United States Patent [19]
Ruschke et al.

[11] Patent Number: 5,674,200
[45] Date of Patent: Oct. 7, 1997

[54] AIR ELIMINATOR

[75] Inventors: Ricky R. Ruschke, McHenry; Tracy L. Leahey, Woodstock; Christine A. Kurtz, Antioch, all of Ill.

[73] Assignee: Filtertek Inc., Hebron, Ill.

[21] Appl. No.: 596,643

[22] Filed: Feb. 5, 1996

[51] Int. Cl.⁶ ............................................. A61M 1/00
[52] U.S. Cl. ........................ 604/126; 604/122; 604/251
[58] Field of Search ............................. 604/7, 27–8, 30, 604/48–9, 51–4, 122–3, 246, 251–2, 255, 322, 325, 403, 406–7, 411–2, 414, 905, 126, 324, 326, 405; 141/18, 59; 210/346, 348, 454, 457, 472, 500.21, 510.1

[56]                References Cited
          U.S. PATENT DOCUMENTS

| | | |
|---|---|---|
| 3,631,654 | 1/1972 | Riely et al. . |
| 3,778,971 | 12/1973 | Granger et al. . |
| 4,004,587 | 1/1977 | Jess ............................. 604/126 |
| 4,143,659 | 3/1979 | Biedermann . |
| 4,198,971 | 4/1980 | Noiles . |
| 4,395,260 | 7/1983 | Todd et al. ........................ 604/122 |
| 4,444,661 | 4/1984 | Jackson et al. . |
| 4,588,403 | 5/1986 | Weiss et al. ...................... 604/411 |
| 4,615,694 | 10/1986 | Raines . |
| 4,900,308 | 2/1990 | Verkaart .......................... 604/406 |
| 4,906,260 | 3/1990 | Emheiser et al. . |
| 5,045,096 | 9/1991 | Quang et al. . |
| 5,102,400 | 4/1992 | Leibinsohn . |
| 5,290,237 | 3/1994 | Verkaart .......................... 604/126 |
| 5,312,352 | 5/1994 | Leschinsky et al. . |
| 5,439,448 | 8/1995 | Leschinsky et al. . |
| 5,468,388 | 11/1995 | Goddard et al. . |

Primary Examiner—Corrine M. McDermott
Assistant Examiner—Bhisma Mehta
Attorney, Agent, or Firm—Brinks Hofer Gilson & Lione

[57]  ABSTRACT

An air elimination device for removing air or gas bubbles from aqueous liquids flowing through an intravenous delivery system. The device comprises a housing having an interior chamber, an inlet passage, an outlet passage, and one or more vent openings. The inlet passage delivers the liquid into the interior chamber. The outlet passage delivers the liquid from the interior chamber. A hydrophobic membrane is attached to the housing and positioned over the vent openings. The hydrophobic membrane allows gas bubbles in the aqueous liquid that enter the interior chamber of the housing to pass through the vent openings while preventing the liquid from passing through the vent openings. The outlet passage comprises a stem which extends inwardly into the interior chamber and terminates in an interior end. The vent openings are shaped and located in the housing such that at least a portion of a vent opening will be positioned at a higher elevation than that of the interior end of the stem irrespective of the orientation of the housing.

18 Claims, 2 Drawing Sheets

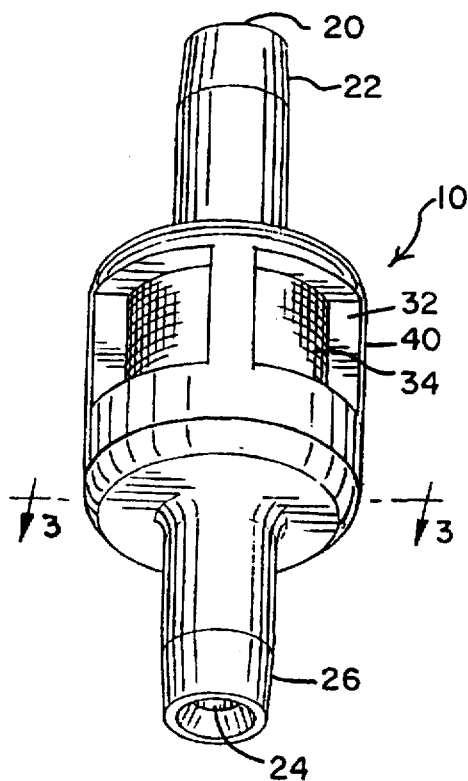
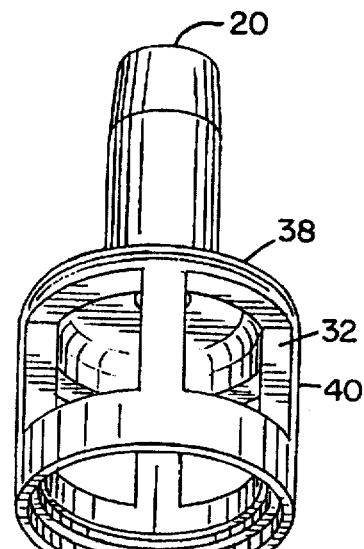
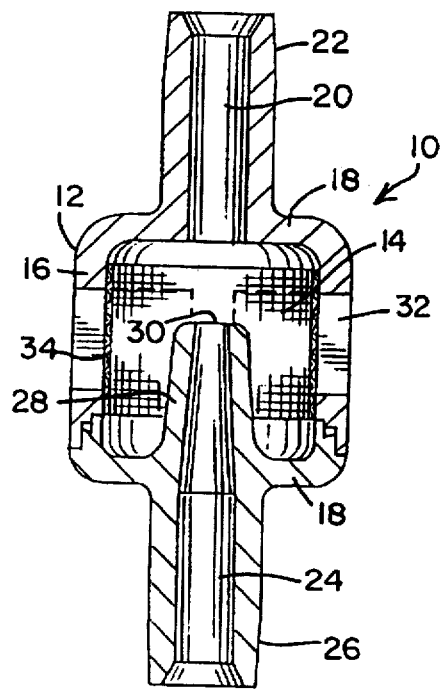
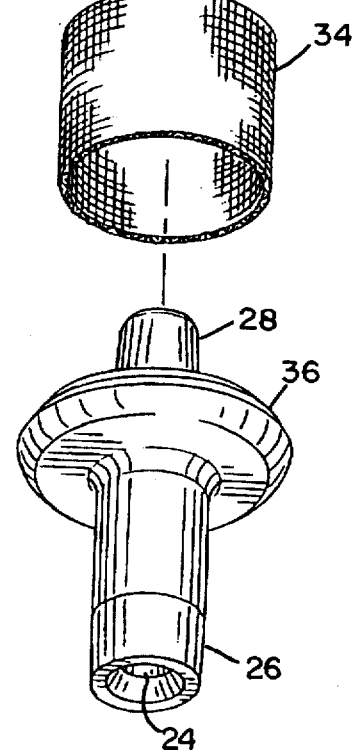

FIG. 5
FIG. 4
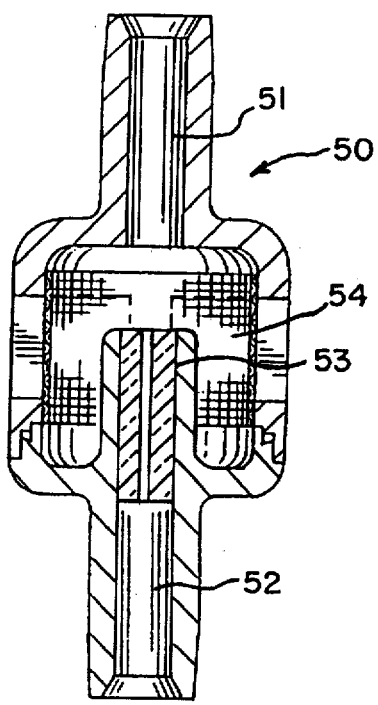
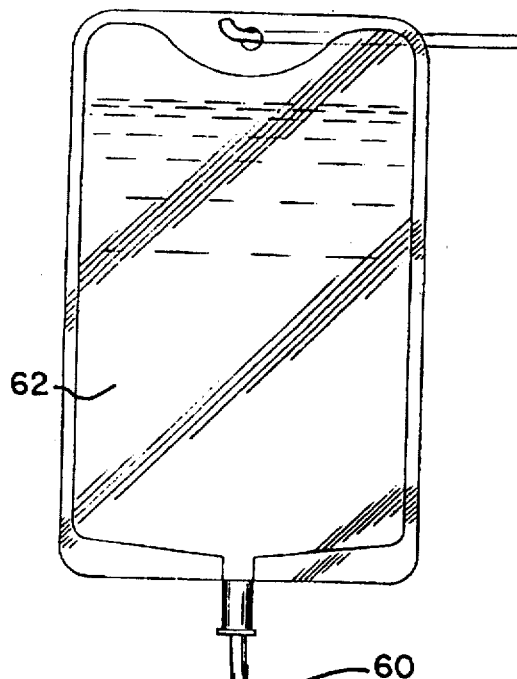
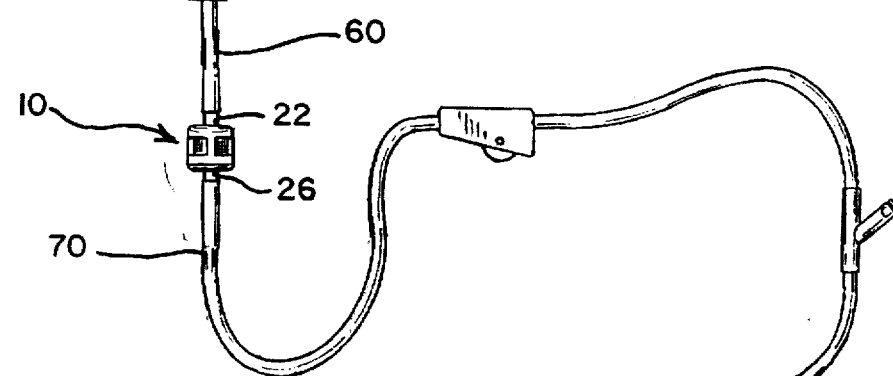
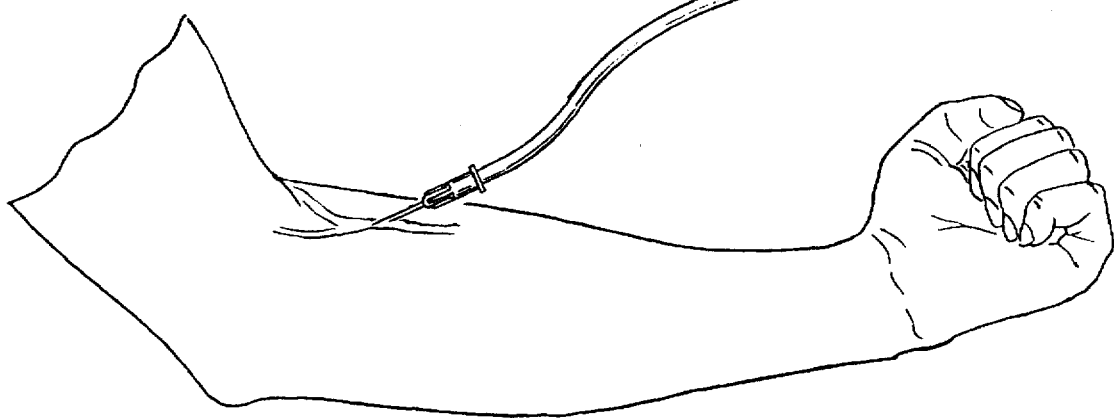

AIR ELIMINATOR

BACKGROUND OF THE INVENTION

The invention relates generally to intravenous delivery systems, and in particular, to low volume drug infusers.

In intravenous delivery systems, it is a common problem for gas bubbles to exist within the solution that is being administered to the patient. For example, most intravenous solutions contain a small percentage of air. In addition, air bubbles often enter the delivery system whenever infusion bottles or other devices are removed, changed, or added. The presence of these gas bubbles can create a number of problems. First, it is important to prevent any gas bubbles from entering the patient's blood stream, where such gas bubbles can cause a gas embolism in the patient. Second, intravenous delivery systems typically utilize a flow control device that contains a small orifice through which the intravenous solution must pass. A gas bubble will often plug the orifice and prevent continued flow of the solution. Third, other devices such as filters may also be impeded by the presence of air.

In the past, individuals have used a filter in the intravenous delivery system where the filter has a vent for expelling gases, such as the filter disclosed in U.S. Pat. No. 4,906,260. Such filters rely on a hydrophilic membrane to positively stop any passage of gas bubbles through the device. The use of these filters to eliminate air has several drawbacks. First, the intravenous solution must pass through the hydrophilic membrane. This can impede the flow of the solution. Second, the use of a filter may be unnecessary, thus adding unwanted costs. Third, some drugs will bind to the hydrophilic membrane and clog the filter, thus completely stopping the flow of the solution. Fourth, the use of a filter may be undesirable when administering certain solutions such as biological drugs or antibiotics where filtration is to be avoided. Nevertheless, it is not uncommon for individuals to employ such filters irrespective of there drawbacks so as to gain the air venting benefits of these filters. It is therefore desirable to provide an effective way of removing air bubbles from intravenous solutions without using hydrophilic filters.

SUMMARY OF THE INVENTION

The invention provides an efficient, low-cost device for removing air or gas bubbles from aqueous liquids flowing through an intravenous delivery system.

The air eliminator device is comprised of a housing having an interior chamber. The housing has one or more vent openings located in the housing adjacent to the interior chamber. A hydrophobic membrane is attached to the housing and positioned over the vent openings. The hydrophobic membrane is capable of allowing gas bubbles in the aqueous liquid to pass through the vent opening while preventing the liquid from passing through the vent openings. The housing comprises an inlet passage for the delivery of the liquid into the chamber. The housing comprises an outlet passage for the delivery of the liquid from the chamber. The outlet passage comprises a stem which extends inwardly into the chamber and terminates in an interior end. The vent openings are shaped and located in the housing such that at least a portion of a vent opening will be positioned at an elevation higher than that of the interior end of the stem irrespective of the orientation of the housing.

As liquid passes into the interior chamber of the device, gas bubbles within the liquid separate and float under the influence of gravity to the upper most portion of the interior chamber. As liquid continues to pass through the device, additional gas bubbles accumulate inside the interior chamber. When sufficient gas has accumulated so as to come in contact with one of the vent openings, the gas will pass through the hydrophobic membrane and the vent opening, thereby exiting the device. The hydrophobic membrane prevents the aqueous liquid from passing through the vent openings.

The inwardly projecting stem functions to prevent gas bubbles within the interior chamber from escaping through the outlet passage before coming into contact with the hydrophobic membrane and one of the vent openings. The stem effectively places the interior opening of the outlet passage at an elevation below that of a vent opening irrespective of the orientation or position of the device. This is of particular importance should the device become inverted (i.e., the outlet passage at an elevation below that of the inlet passage). Consequently, the air eliminator device is not position sensitive.

The above device is simple and inexpensive to manufacture. This is of particular importance since these devices are typically disposed of after each use. The device also eliminates the need for a hydrophilic filter to positively block the passage of gas bubbles. Hydrophilic filters are relatively expensive and can impede or even prevent the flow of liquid through the intravenous delivery system. Moreover, hydrophilic filters are undesirable for the administration of certain types of biological drugs and antibiotics.

These together with other objects and advantages which will become apparent in the details of construction and operation as more fully described and claimed below.

BRIEF DESCRIPTION OF THE DRAWINGS

FIG. 1 is a perspective view of the air eliminator device.

FIG. 2 is an exploded perspective view of the air eliminator device showing the component elements thereof.

FIG. 3 is a cross-sectional view taken along line 3—3 of FIG. 1.

FIG. 4 is a cross-sectional view of an alternative embodiment of the air eliminator similar to the view of FIG. 3.

FIG. 5 is a perspective view of the air eliminator device being employed as part of an intravenous delivery system.

DETAILED DESCRIPTION OF THE DRAWINGS AND PREFERRED EMBODIMENTS OF THE INVENTION

Referring to FIGS. 1 and 3 of the drawings, reference numeral 10 indicates in general the preferred air eliminator device of the present invention. The air eliminator device 10 is comprised of a housing 12 having an interior chamber 14. In the preferred embodiment shown, the housing 12 is comprised of a cylindrical side wall 16 and two opposing end walls 18. The housing 12 should be made of a material, preferably plastic, which will not react with or contaminate the aqueous liquid passing through the device. To avoid the collection of unwanted materials within the device, the interior surface of the housing 12 should be free of any corners or sharp angles. In the preferred embodiment shown, a radius is provided at the juncture of the housing side wall 16 and the opposing end walls 18.

An inlet passage 20 is provided on the housing 12 for delivery of liquids into the interior chamber 14 of the housing. The inlet passage 20 includes an inlet port 22 which protrudes from the housing 12. An outlet passage 24 is also provided on the housing 12 for delivery of liquids from the interior chamber 14 of the housing. The outlet passage 24 includes an outlet port 26 which protrudes from the housing 12. The inlet passage 20 and the outlet passage 24 are of sufficient diameter to allow unobstructed flow of the aqueous liquid being administered. In the preferred embodiment shown, the inlet port 22 and the outlet port 26 are located on opposite end walls 18 of the housing and are designed to be connected to standard IV tubing 60 (FIG. 5) used in intravenous delivery systems.

The outlet passage 24 also comprises a stem 28 which extends inwardly into the interior chamber 14. In the preferred embodiment shown, the stem 28 extends to the approximate center of the interior chamber 14. In addition, the cross-sectional area of the outlet passage 24 at the interior end of the stem 30 is preferably less than the cross-sectional area of the inlet passage 20.

One or more vent openings 32 are located in the housing 12 adjacent to the interior chamber 14. The vent openings 32 are positioned in such a manner that at least a portion of a vent opening will always be at a higher elevation than the interior end of the stem 30, irrespective of the orientation of the housing 12. The vent openings 32 are of sufficient size to allow gas bubbles in the aqueous liquid to escape the housing 12. In the preferred embodiment shown, a plurality of vent openings 32 are located along the perimeter of the housing side wall 16 and are separated by ribs 40. The ribs 40 provide strength and rigidity to the housing 12 and also help support the hydrophobic membrane 34, described below.

A hydrophobic membrane 34 is attached to the housing 12 and positioned over the vent openings 32. The hydrophobic membrane 34 allows the passage of gas bubbles in the aqueous liquid that enters the interior chamber 14 to pass through the vent openings 32 and escape from the housing 12. The hydrophobic membrane 34, however, prevents the passage of the aqueous liquid contained in the interior chamber 14 from escaping through the vent openings 32. The pressure of the aqueous liquid passing through the air eliminator device prevents outside air from passing through the hydrophobic membrane 34 and entering into the intravenous delivery system. The hydrophobic membrane 34 preferably has a pore size of 0.2–3.0 microns and extends continuously along the perimeter of the housing side wall 16. The hydrophobic membrane of the preferred embodiment is comprised of a Versapor Grade R membrane having a 0.2 micron pore size, manufactured by the Gelman Corporation.

Referring to FIG. 4 of the drawings, the outlet passage 52 of an alternative embodiment of the air eliminator device 50 comprises a flow control device 53. The flow control device 53 is preferably a glass tube having an orifice with a interior cross-sectional area substantially less than the cross-sectional area of the inlet passage 51.

Referring to FIG. 2 of the drawings, the preferred embodiment shown is manufactured as follows. The housing 12 is manufactured from two separate parts, the outlet housing 36 and the inlet housing 38, respectively. Both the outlet housing 36 and the inlet housing 38 are preferably injection molded from plastic. The hydrophobic membrane 34 is insert molded into the inlet housing 38, thereby sealing the edges of the membrane to the interior surface of the housing. The inlet housing 38 is then welded to the outlet housing 36, preferably by ultrasonic or spin welding, to complete the assembly of the air eliminator device. If the outlet passage 24 comprises a flow control device such as a glass tube 53 (FIG. 4), the flow control device is preferably pressed or molded into the outlet passage 52.

Referring to FIG. 5 of the drawings, the preferred air eliminator device 10 operates as follows. The air eliminator device 10 is typically installed in an intravenous delivery system, such as a low volume drug infuser, by connecting the IV set tubing 60 from the aqueous liquid source 62 to the inlet port 22. IV tubing 70 leading to the patient is then connected to the outlet port 26. The air eliminator device is ordinarily, although not necessarily, positioned in a more or less vertical orientation with the inlet passage 20 located above the outlet passage 24. Any devices which can be affected by air bubbles, such as flow control regulators, drip chambers, or filters, are preferably located downstream from the air eliminator device. The system is then primed with the aqueous liquid to be administered to remove the air in the IV tubing and other devices before connecting the delivery system to the patient.

During administration of the aqueous liquid to the patient, the liquid first passes through the air eliminator device 10. Referring to FIG. 3 of the drawings, the liquid enters the interior chamber 14 of the device through the inlet passage 20. As the liquid enters the interior chamber 14, any gas bubbles within the liquid tend to separate from the liquid and rise or float under the influence of gravity to the upper most portion of the interior chamber 14 near the end wall 18 adjacent to the inlet passage 20. The increased cross-sectional area of the interior chamber 14 as compared to the cross-sectional area of the inlet passage 20 and the outlet passage 24 cause a decreased rate of flow of the liquid through the interior chamber 14, thereby promoting the separation of gas bubbles from the liquid. The aqueous liquid, free of gas bubbles, then leaves the interior chamber 14 by passing through the outlet passage 24.

As the aqueous liquid flows through air eliminator device 10, gas bubbles continue to accumulate in the upper most portion of the interior chamber 14. When sufficient gas has accumulated to come in contact with the hydrophobic membrane 34 and, consequentially, one of the vent openings 32, the gas will pass through the hydrophobic membrane 34 and the vent opening 32, thereby exiting the intravenous delivery system. The pressure within the aqueous liquid that exists under normal operation of the delivery system assists in expelling the gas through the hydrophobic membrane 34. The hydrophobic membrane 34 prevents the aqueous liquid from escaping through the vent openings 32 of the device.

It may be desirable to decrease the cross-sectional area of the outlet passage 24 as compared to the cross-sectional area of the inlet passage 20, particularly for use in high flow intravenous delivery systems. Decreasing the cross-sectional area of the outlet passage 24 will increase the pressure of the aqueous liquid inside the interior chamber 14. This increased pressure will increase the rate at which gas bubbles will pass through the hydrophobic membrane 34 and vent openings 32.

Referring to FIG. 3 of the drawings, the pressure of the aqueous liquid inside the interior chamber 14 can be increased by reducing the cross-sectional area of the outlet passage 24 at the interior end of the stem 30. For example, in the preferred embodiment shown, the interior diameter of the inlet passage 20 is 0.090 inches and the interior diameter of the interior end of the stem 30 is 0.040–0.060 inches.

Referring to FIG. 4 of the drawings, the pressure of the aqueous liquid inside the interior chamber 54 can also be increased by inserting a flow control device 53 into the outlet passage 52. In the alternative embodiment shown, the flow control device 53 is preferably a glass tube having an orifice of 0.0015–0.020 inches in diameter.

Although the air eliminator device 10 is ordinarily positioned in a more or less vertical orientation with the inlet passage 20 located above the outlet passage 24, the device will also function in a horizontal or inverted position. For example, if the device is inverted so that the outlet passage 24 is above the inlet passage 20, gas bubbles within the liquid will still rise to the upper most portion of the interior chamber 14, in this case, near the end wall 18 adjacent to the outlet passage 24. The outlet stem 28 prevents the bubbles from passing through the outlet passage 24 by positioning the interior end of the stem 30 below the accumulated gas in the interior chamber 14. As described above, when sufficient gas has accumulated to come in contact with the hydrophobic membrane 34, and consequentially one of the vent openings 32, the gas will pass through the hydrophobic membrane 34 and the vent opening 32, thereby exiting the intravenous delivery system. The stem 28 must project inwardly into the interior chamber 14 a sufficient distance to prevent accumulated gas from coming into contact with the interior end of the stem 30 prior to coming into contact with the vent openings 32.

Although it is possible for a gas bubble to rise from the inlet passage 20 and directly enter the stem 28 when the air eliminator device 10 is in the inverted position, this possibility has been substantially eliminated by reducing the cross-sectional area of the interior end of the stem 30 as compared to the cross-sectional area of the inlet passage 20. Gas bubbles entering through the inlet passage 20 typically have a diameter corresponding to the diameter of the inlet passage 20. These gas bubbles will generally be too large to enter the stem 28. Thus, any gas bubbles that strike the interior end of the stem 30 will typically deflect off to the side and accumulate in the upper most portion of the interior chamber 14 adjacent to the base of the stem 28.

When the air eliminator device 10 is in the horizontal position, gas bubbles will tend to accumulate against upper most portion of the housing side wall 16. From there, the gas will readily exit the device 10 through the hydrophobic membrane 34 and one of the vent openings 32. The position of the interior end of the stem 30 below the vent opening 32 in the upper most portion of the housing side wall 16 prevents the accumulated gas from passing through the outlet passage 24.

As can be seen from the above description, the air eliminator device will effectively eliminate gas bubbles from an aqueous liquid irrespective of the orientation or position of the device.

It should be appreciated that any number of configurations or arrangements for the various components described above may be utilized to accomplish the invention claimed herein. For example, the vent openings could be located in the end walls 18 adjacent to the inlet and outlet passages, 20 and 24 respectively. In addition, the inlet and outlet passages, 20 and 24 respectively, could be located in the same end wall 18. Likewise, the housing 12 can be of any geometric shape, such as a cube or a sphere.

We claim:

1. A device for removing gas bubbles from liquids in intravenous delivery systems comprising:

a) a housing having an interior chamber for receiving liquid passing through the device, said housing having a vent opening on the periphery of the chamber;

b) a hydrophobic membrane attached to said housing and positioned over said vent opening, said hydrophobic membrane capable of allowing gas bubbles in the liquid to pass through said vent opening while preventing aqueous liquid from passing through said vent opening;

c) an inlet passage to the housing, said inlet passage being fluidly contiguous with the chamber for delivering the liquid directly into the chamber;

d) an outlet passage to the housing, said outlet passage being fluidly contiguous with the chamber for delivering any liquid accumulated in the chamber directly from the chamber, said outlet passage comprising a stem which extends said outlet passage inwardly into the chamber and terminates in an interior end; and e) said vent opening being shaped and located in the housing such that at least a portion of the vent opening will be positioned at an elevation higher than that of the interior end of the stem irrespective of the orientation of the housing.

2. A device according to claim 1, wherein the cross-sectional area of the outlet passage is smaller than the cross-sectional area of the inlet passage to increase the pressure of the liquid in the interior chamber as liquid flows through the interior chamber.

3. A device according to claim 2, further comprising a flow control device in the outlet passage and having an orifice of 0.0015–0.020 inches in diameter.

4. A device according to claim 3, wherein said flow control device is comprised of a glass tube.

5. A device according to claim 1, wherein said housing comprises a plurality of vent openings, said hydrophobic membrane being positioned over said vent openings, said vent openings being shaped and located such that at least a portion of a vent opening will be positioned at an elevation higher than that of the interior end of the stem irrespective of the orientation of the housing.

6. A device according to claim 3, wherein said hydrophobic membrane extends continuously in the form of a band along the periphery of the housing.

7. A device according to claim 1, wherein said housing comprises a cylindrical side wall and opposing end walls, said inlet passage is located in one of the housing end walls, said outlet passage is located in the opposite housing end wall, and said vent opening is located in the housing side wall.

8. A device according to claim 7, wherein said housing comprises a plurality of vent openings located along the perimeter of the housing side wall, said hydrophobic membrane being positioned over said vent openings, said vent openings being shaped and located such that at least a portion of a vent opening will be positioned at an elevation higher than that of the interior end of the stem irrespective of the orientation of the housing.

9. A device according to claim 7, wherein said hydrophobic membrane extends continuously in the form of a band along the perimeter of the housing side wall.

10. A device according to claim 7, wherein said housing is plastic.

11. A device according to claim 1, wherein the interior end of the stem is located at the approximate center of the interior chamber.

12. A device according to claim 1, wherein the cross-sectional area of the outlet passage at the interior end of the stem is less than the cross-sectional area of the inlet passage.

13. A device according to claim 1, wherein said hydrophobic membrane is comprised of a membrane having a pore size of 0.2–3.0 microns.

14. A device according to claim 1, wherein said inlet passage and said outlet passage each comprise an IV tubing connector.

15. A device according to claim 1, wherein said housing comprises opposing end walls, said inlet passage is located in one of the housing end walls and said outlet passage is located in the opposite housing end wall.

16. A device for removing gas bubbles from liquids in intravenous delivery systems comprising:

a) a housing comprising a side wall and opposing first and second end walls defining an interior chamber, said interior chamber for receiving liquid passing through the device, said housing having a plurality of vent openings along the perimeter of the side wall;

b) a hydrophobic membrane attached to said housing and positioned over said vent openings, said hydrophobic membrane capable of allowing gas bubbles in the liquid to pass through said vent opening openings while preventing aqueous liquid from passing through said vent opening openings;

c) an inlet passage located in said first end wall of the housing, said inlet passage being fluidly contiguous with the chamber for delivering the liquid directly into the chamber, said inlet passage comprising an IV tubing connector extending outwardly from the first housing end wall;

d) an outlet passage located in the second end wall of the housing, said outlet passage being fluidly contiguous with the chamber for delivering any liquid accumulated in the chamber directly from the chamber, said outlet passage comprising a stem and a IV tubing connector, said IV tubing connector extending outwardly from the second housing end wall, said stem extending said outlet passage inwardly into the interior chamber and terminating in an interior end located at the approximate center of the interior chamber, said outlet passage further comprising a flow control device; and e) said plurality of vent openings being shaped and located in the housing such that at least a portion of a vent opening will be positioned at an elevation higher than that of the interior end of the stem irrespective of the orientation of the housing.

17. A device according to claim 16, wherein said flow control device is comprised of a glass tube having an orifice of 0.0015–0.020 inches in diameter.

18. A device for removing gas bubbles from liquids in intravenous delivery systems comprising:

a) a housing comprising a side wall and opposing first and second end walls defining an interior chamber, said interior chamber for receiving liquid passing through the device, said housing having a plurality of vent openings along the perimeter of the side wall;

b) a hydrophobic membrane attached to said housing and positioned over said vent openings, said hydrophobic membrane capable of allowing gas bubbles in the liquid to pass through said vent opening openings while preventing aqueous liquid from passing through said vent opening openings;

c) an inlet passage located in said first end wall of the housing, said inlet passage being fluidly contiguous with the chamber for delivering the liquid directly into the chamber, said inlet passage comprising an IV tubing connector extending outwardly from the first housing end wall;

d) an outlet passage located in the second end wall of the housing, said outlet passage being fluidly contiguous with the chamber for delivering any liquid accumulated in the chamber directly from the chamber, said outlet passage comprising a stem and a IV tubing connector, said IV tubing connector extending outwardly from the second housing end wall, said stem extending said outlet passage inwardly into the interior chamber and terminating in an interior end located at the approximate center of the interior chamber, said outlet passage having a cross-sectional area at the interior end of the stem less than the cross-sectional area of the inlet passage; and e) said plurality of vent openings being shaped and located in the housing such that at least a portion of a vent opening will be positioned at an elevation higher than that of the interior end of the stem irrespective of the orientation of the housing.

* * * * *